US005917021A

United States Patent [19]

Lee

[11] Patent Number: 5,917,021
[45] Date of Patent: Jun. 29, 1999

[54] STABILIZED MONOMERIC PROTEIN COMPOSITIONS

[75] Inventor: Lihsyng Stanford Lee, Princeton Junction, N.J.

[73] Assignee: Enzon, Inc., Piscataway, N.J.

[21] Appl. No.: 08/819,033

[22] Filed: Mar. 17, 1997

Related U.S. Application Data

[63] Continuation of application No. 08/417,855, Apr. 7, 1995, Pat. No. 5,656,730.
[51] Int. Cl.$^6$ .......................... A61K 39/395; C07K 16/00
[52] U.S. Cl. ...................................... 530/387.3; 530/387.7; 530/390.5; 424/133.1; 424/135.1; 435/69.6; 435/69.7; 435/328
[58] Field of Search .............................. 530/387.3, 387.7, 530/390.5; 435/69.6, 69.7, 172.1, 172.3; 424/133.1, 135.1, 155.11

[56] References Cited

U.S. PATENT DOCUMENTS

| | | | |
|---|---|---|---|
| 3,950,513 | 4/1976 | Jenson | 424/94 |
| 4,496,537 | 1/1985 | Kwan | 424/85 |
| 4,597,966 | 7/1986 | Zolton et al. | 424/85 |
| 4,645,830 | 2/1987 | Yasushi et al. | 530/351 |
| 4,704,692 | 11/1987 | Ladner | 364/496 |
| 4,777,043 | 10/1988 | Bennett et al. | 424/94.64 |
| 4,806,524 | 2/1989 | Kawaguchi et al. | 514/8 |
| 4,946,778 | 8/1990 | Ladner et al. | 435/69.6 |
| 5,096,885 | 3/1992 | Pearlman et al. | 514/12 |
| 5,260,203 | 11/1993 | Ladner et al. | 435/172.3 |
| 5,358,708 | 10/1994 | Patel | 424/85.1 |
| 5,591,828 | 1/1997 | Boslet et al. | 530/387.3 |
| 5,644,030 | 7/1997 | Faulmann | 530/350 |

FOREIGN PATENT DOCUMENTS

| | | |
|---|---|---|
| 57-26587 | 2/1982 | Japan . |
| 59-181224 | 10/1984 | Japan . |
| 700132 | 11/1979 | U.S.S.R. . |

OTHER PUBLICATIONS

Adams, G.P., et al., "Highly Specific in Vivo Tumor Targeting by Monovalent and Divalent Forms of 741F8 Anti--c--erbB--2 Single--Chain Fv," *Cancer Res.* 53:4026–4034 (1993).

Buchner, J., and Rudolph, R., "Renaturation, Purification and Characterization of Recombinant F$_{ab}$–Fragments Produced in *Escherichia coli*," *Bio/Technology* 9:157–162 (1991).

Buchner, J., et al., "A Method for Increasing the Yield of Properly Folded Recombinant Fusion Proteins: Single–Chain Immunotoxins from Renaturation of Bacterial Inclusion Bodies," *Anal. Biochem.* 205:263–270 (1992).

Colcher, D., et al., "In Vivo Tumor Targeting of a Recombinant Single–Chain Antigen–Binding Protein," *J. Natl. Cancer Inst.* 82:1191–1197 (1990).

Colombo, M.F., et al., "Protein Solvation in Allosteric Regulation: A Water Effect on Hemoglobin," *Science* 256:655–659 (1992).

Crowe, J.H., et al., "Stabilization of dry phospholipid bilayers and proteins by sugars," *Biochem. J.* 242:1–10 (1987).

Holliger, P., et al., ""Diabodies": Small bivalent and bispecific antibody fragments," *Proc. Natl. Acad. Sci. USA* 90:6444–6448 (1993).

Lee, L. Stanford, "Protein Folding and Polymerization Study with a Recombinant Single Chain Antibody," *FASEB J.* 9:A410 (Abstract 2377) (Mar. 1995).

Levine, R.L., "Oxidative Modification of Glutamine Synthetase. II. Characterization of the Ascorbate Model System," *J. Biol. Chem.* 258:11828–11833 (1983).

Mézes, P.S., et al., "Molecular Design of Anti–Tumor Single Chain Fv Species," Third Annual IBC International Conference on Antibody Engineering, San Diego, CA (1992) (one page).

Milenic, D.E., et al., "Construction, Binding Properties, Metabolism, and Tumor Targeting of a Single–Chain Fv Derived from the Pancarcinoma Monoclonal Antibody CC49," *Cancer Res.* 51:6363–6371 (1991).

Müller, J.D., and Nienhaus, G.U., "Ligand Binding to Anti–Fluorescyl Antibodies: Stability of the Antigen Binding Site," *Biochemistry* 33:6221–6227 (May 1994).

Newton, D.L., et al., "Expression and Characterization of Recombinant Human Eosinophil–derived Neurotoxin and Eosinophil–derived Neurotoxin–Anti–transferrin Receptor sFv," *J. Biol. Chem.* 269:26739–26745 (Oct. 1994).

Pantoliano, M.W., et al., "Conformational Stability, Folding, and Ligand–Binding Affinity of Single–Chain Fv Immunoglobulin Fragments Expressed in *Escherichia coli*," *Biochemistry* 30:10117–10125 (1991).

Rand, R.P., "Raising Water to New Heights," *Science* 256:618 (1992).

Sawyer, J.R., et al., "The effects of induction conditions on production of a soluble anti–tumor sFv in *Escherichia coli*," *Protein Engineering* 7:1401–1406 (Nov. 1994).

Wang, Y.J., and Hanson, M.A., "Parenteral Formulations of Proteins and Peptides: Stability and Stabilizers," *J. Parenteral Sci. and Technol.* 42(Suppl.):S4–S26 (1988).

(List continued on next page.)

*Primary Examiner*—Julie Reeves
*Attorney, Agent, or Firm*—Sterne, Kessler, Goldstein & Fox P.L.L.C.

[57] ABSTRACT

The present invention relates to a stabilized protein composition comprising a monomeric protein and a storage-stabilizing amount of sucrose, histidine or glycine, which is sufficient to inhibit aggregation of the protein molecules during freeze/thaw cycles, and methods therefor. More particularly, this invention relates to pharmaceutically-acceptable, single-chain antigen-binding protein compositions having increased frozen-storage stability, especially to freeze/thaw cycles.

13 Claims, No Drawings

OTHER PUBLICATIONS

Weidner, K.M., et al., "Molecular Stabilization Effects of Interactions between Anti–metatype Antibodies and Liganded Antibody," *J. Biol. Chem.* 267:10281–10288 (1992).

Whitlow, M., and Filpula, D., "Single–Chain Fv Proteins and Their Fusion Proteins," *Methods* 2:97–105 (1991).

Whitlow, M., et al., "An improved linker for single–chain Fv with reduced aggregation and enhanced proteolytic stability," *Protein Engineering* 6:989–995 (1993).

Whitlow, M., et al., "Multivalent Fvs: characterization of single–chain Fv oligomers and preparation of a bispecific Fv," *Protein Engineering* 7:1017–1026 (Aug. 1994).

Harlow et al Anitbodies: A laboratory Manual Cold Spring Harbor Laboratory Chapter 12, pp. 498 and 549, 1988.

Webster's II New Riverside University Dictionary, The Riverside Publishing House pp. 120,505, 509, 697, 1199, 1303, 1994.

STABILIZED MONOMERIC PROTEIN COMPOSITIONS

This application is a continuation of application Ser. No. 08/417,855, filed Apr. 7, 1995, that issued on Aug. 12, 1997 as U.S. Pat. No. 5,656,730.

FIELD OF THE INVENTION

The present invention relates to a stabilized protein composition comprising a monomeric protein and a storage-stabilizing amount of sucrose, histidine or glycine, which is sufficient to inhibit aggregation of the protein molecules during freeze/thaw cycles, and methods, therefor. More particularly, this invention relates to pharmaceutically acceptable, monomeric single-chain antigen-binding protein compositions having increased frozen-storage stability, especially to freeze/thaw cycles.

BACKGROUND OF THE INVENTION

The useful lifetime of proteins, particularly those developed for pharmaceutical administration, is extended by storage as frozen, lyophilized or refrigerated aqueous compositions. However, upon thawing, frozen non-lyophilized monomeric proteins have a tendency to form polymeric aggregates. Although the formation of a multivalent compound may be desirable in specific situations, unwanted aggregation is disadvantageous in a monomeric protein composition.

Antibodies represent a specific class of proteins generated by the immune system to provide a molecule capable of complexing with an invading molecule, termed an antigen. Natural antibodies have two identical antigen-binding sites, both of which are specific to a particular antigen. The antibody molecule "recognizes" the antigen by complexing its antigen-binding sites with areas termed epitopes. The epitopes fit into the conformational architecture of the antigen-binding sites of the antibody, enabling the antibody to bind to the antigen.

The antibody molecule is composed of two identical heavy and two identical light chains, held together by disulfide bonds. Covalent interchain and intrachain bonding serves to stabilize the various chains of antibody molecules.

The light chain comprises one variable region (termed $V_L$) and one constant region ($C_L$), while the heavy chain comprises one variable region (termed $V_H$) and three constant regions ($C_H1$, $C_H2$ and $C_H2$). Pairs of regions associate to form discrete structures. The light-chain variable region, $V_L$, and the heavy-chain variable region, $V_H$, of a particular antibody molecule have specific amino acid sequences that allow the antigen-binding site to assume a conformation that binds to the antigen epitope recognized by that particular antibody. More specifically, the light and heavy chain variable regions, $V_L$ and $V_H$ associate to form an "$F_v$" area which contains the antigen-binding site.

Cleavage of the naturally-occurring antibody molecule with a proteolytic enzyme generates fragments which retain their antigen binding site. Fragments of this type, commonly known as Fab (for Fragment, antigen binding) are composed of the $C_L$, $V_L$, $C_H1$ and $V_H$ regions of the antibody, wherein the light chain and the fragment of the heavy chain are covalently linked by a disulfide linkage.

Recent advances in immunobiology, recombinant DNA technology, and computer science have allowed the creation of single polypeptide chain molecules that bind antigen. These single-chain antigen-binding molecules contain only the variable domains of the antibody, incorporating a linker polypeptide to bridge the variable regions, $V_L$ and $V_H$, into a single, monomeric polypeptide chain, the "$sF_v$." A computer-assisted method for linker design is described more particularly in U.S. Pat. No. 4,704,692. A description of the theory and production of single-chain antigen-binding proteins is found in U.S. Pat. Nos. 4,946,778 and 5,260,203. The single-chain antigen-binding proteins produced under the process recited in U.S. Pat. Nos. 4,946,778 and 5,260,203 have binding specificity and affinity substantially similar to that of the corresponding Fab fragment. Several different single-chain molecules that can successfully bind antigen have now been constructed using a variety of peptide linkers. For a review, see Whitlow and Filpula, *Methods: Compan. Methods Enzymol.* 2:97–105 (1991).

Many of the early single-chain $F_v$ products were insoluble aggregates, requiring solubilization under strong denaturing solutions, followed by renaturing and proper refolding before they could manifest single-chain antigen binding ability. See, e.g., Buchner et al., *Bio/Technol.* 9:157 (1991) and Buchner et al., *Analyt. Biochem.* 205:263 (1992). Thus, it has been found to be particularly advantageous to provide for the expression of a single-chain antigen-binding molecule as a soluble product, which can be purified directly from the periplasmic fraction without the need for in vitro manipulation and refolding. See, Sawyer et al., *Protein Engineering* 7:1401 (1994).

However, if the soluble, monomeric protein composition forms aggregates during frozen storage of the non-lyophilized product, or as a result of the freeze/thaw process, a heterogeneous, unstable composition may result in which immunoreactivity may be diminished. At the very least, disadvantageous aggregation of the protein monomers as a result of storage instabilities may require additional purification steps (including denaturation and refolding) to restore the protein to a composition of homogeneous monomers. Biological consistency and stability are essential for most clinical applications of a monomeric, single-chain antigen-binding protein composition.

Studies have been made, at both the academic and clinical levels, of the decomposition mechanisms of proteins. As a result, the art has recognized that different proteins exhibit highly variable inactivation responses. For example, R. L. Levine has reported in *J. Biol. Chem.* 258:11828 (1983) an analysis of the effects of 24 amino acids and sulfhydryl compounds as stabilizers to inhibit glutamine synthetase degradation in a system containing oxygen, ascorbate and trace metal. Levine disclosed that only cysteine and histidine showed significant activity in preventing loss of activity for the enzyme, whereas some of the compounds tested actually stimulated the inactivation reaction. For instance, the inactivation of the enzyme creatine kinase by ascorbate has been shown to be stimulated by histidine.

Several authors have described methods for stabilizing a lyophilized protein composition. For example, in U.S. Pat. No. 4,496,537, Kwan describes the enhanced storage stability of lyophilized alpha-type interferon formulations, by incorporating glycine or alanine prior to lyophilization. The resulting lyophilized formulations can be stored without loss of activity for more than six months at 20° C. before reconstitution with water.

An abstract of Japanese Patent Application 59-181224 discloses an enhanced stability for interferons having added an amino acid and, optionally, human serum albumin before freeze drying. Yasushi et al. disclose in U.S. Pat. No. 4,645,830, that interleukin-2 is stabilized against loss of activity during freezing, lyophilization or storage, by formulating the composition to include human serum albumin, a reducing compound or both, and by adjusting the pH to between 3 and 6. According to Yasushi et al., the interleukin-2 formulation may also contain an amino acid, particularly glycine, a monosaccharide, and/or a sugar alcohol.

To avoid the inconvenience of reconstituting a lyophilized product and because of the potential for introducing an error during such procedures, other authors have analyzed methods for stabilizing a refrigerated, aqueous protein composition. An abstract of Japanese Patent Application 57-26587 describes the stabilization of ascorbic acid oxidase by adding one or more of the following: arginine, lysine, histidine and borates. In addition, in U.S. Pat. No. 4,806,524, Kawaguchi et al. describe the stabilization of either freeze-dried or aqueous erythropoietin formulations against decomposition, by adding one or more of the following: polyethylene glycol, proteins, sugars, amino acids, inorganic salts, organic salts and sulfur-containing reducing agents. Furthermore, in U.S. Pat. No. 4,777,043, Bennett et al. report that an increased solubility and stability is obtained when human tissue plasminogen activator is formulated to contain arginine, as the protonated cation "argininium ion."

More recently, Patel, in U.S. Pat. No. 5,358,708, has disclosed a method for increasing the storage stability of an aqueous formulation containing a protein component selected from among the group consisting of interferons, granulocyte-macrophage colony-stimulating factors and interleukins, by the addition of a stabilizing amount of methionine, histidine or mixtures thereof. Patel reports that without such treatment, aqueous protein formulations typically have short useful storage lives after reconstitution, even when stored at low temperatures (e.g., 5° C.).

Finally, certain authors have described particular methods for the stabilization of protein compositions designed specifically for pharmaceutical applications. According to Jensen in U.S. Pat. No. 3,950,513, the solubility and stability of plasmin solutions for parenteral administration are enhanced by the addition of physiologically non-toxic amino acids. While, in Technical Report No. 10, entitled "Parenteral Formulations of Proteins and Peptides: Stability and Stabilizers," *J. Parenteral Sci. & Technol.* 42:S12-S13, Supplement 1988, Y-C. J. Wang and M. A. Hanson review the use of amino acids to stabilize parenteral formulations of proteins and peptides.

Recent publications have reported that besides the protein structure itself, the surrounding solvent shell is of crucial importance for the stability and dynamic properties of the protein composition. See Muller et al. *Biochemistry* 33:6221 (1994). Moreover, even the role of water in protein aggregation and protein reactions has received considerable attention (Rand, *Science* 256:618 (1992); Colombo et al., *Science* 256:655 (1992).

A number of investigators have reported the spontaneous aggregation of $sF_v$s. Weidner et al., *J. Biol. Chem.* 267:10281 (1992) observed aggregates of the 4-4-20/212 $sF_v$; Mezes et al., Third Annual IBC Intern'l Conf. on Antibody Engineering, San Diego, Calif. (1992) reported aggregates of the CC49/205c $sF_v$; Adams et al., *Cancer Res.* 53:4026 (1993) and Hollinger et al., *Proc. Nat'l Acad. Sci. USA* 90:6444 (1993) described divalent $sF_v$ of anti-c-erbB-2 $sF_v$; and Whitlow et al, *Protein Eng.* 7:1017 (1994) investigated heterodimers of the CC49 and 4-4-20 $sF_v$s.

However, until the discovery of the present invention, there remained a long-felt need in the art for a method of stabilizing frozen, non-lyophilized, monomeric protein compositions to inhibit or prevent unwanted aggregation of the soluble polypeptide molecules, particularly when the composition is exposed to repeated freeze/thaw cycles. Therefore, the invention of the presently formulated, stabilized protein composition, its method of preparation, and pharmaceutically-acceptable compositions prepared thereby will significantly advance the art by ensuring a stable supply of such proteins as consistent, essentially homogeneous monomers.

SUMMARY OF THE INVENTION

In view of the importance of maintaining a consistent, essentially homogeneous supply of storage-stable protein compositions, the present invention relates to a stabilized protein composition comprising a monomeric single-chain antigen-binding protein and a storage-stabilizing amount of sucrose, histidine or glycine, which is sufficient to inhibit aggregation of the protein monomers as a result of frozen storage. Moreover, the stabilized monomeric single-chain antigen-binding protein composition comprising a storage-stabilizing amount of sucrose, histidine or glycine will withstand repeated freeze/thaw cycles without significant aggregation of the polypeptide molecules.

Accordingly, the invention is directed to a sucrose, histidine or glycine storage-stabilized monomeric single-chain antigen-binding protein formulation, its method of preparation, and pharmaceutically-acceptable compositions prepared thereby.

Also provided is a method of inhibiting aggregation of a monomeric single-chain antigen-binding protein composition in frozen storage comprising adding a storage-stabilizing amount of sucrose, histidine or glycine, wherein the resulting protein composition will withstand repeated freeze/thaw cycles without significant aggregation of the peptide molecules.

Preferably, the invention provides a method of inhibiting aggregation of a monomeric single-chain antigen-binding protein composition comprising adding a frozen storage-stabilizing amount of histidine. The thus provided stabilized monomeric protein composition will withstand repeated freeze/thaw cycles without significant aggregation of the peptide molecules.

Another aspect of the invention includes the storage-stabilized monomeric protein product of the above-disclosed method of inhibiting aggregation.

A further aspect of the invention is a pharmaceutically-acceptable, storage-stabilized, protein composition comprising a monomeric single-chain antigen-binding protein and an amount of sucrose, histidine or glycine which is sufficient to inhibit aggregation of said monomers during frozen storage and a pharmaceutically acceptable buffer therefor. Preferably, the invention provides a pharmaceutically-acceptable, frozen storage-stabilized monomeric protein composition comprising the single-chain antigen-binding protein and a storage-stabilizing amount of histidine, so that the resulting protein composition will withstand repeated freeze/thaw cycles without significant aggregation of the polypeptide molecules.

Other aspects, objects, features and characteristics of the present invention will become more apparent upon consideration of the following description and appended claims.

DETAILED DESCRIPTION OF THE PREFERRED EMBODIMENTS

This invention relates to the discovery that the inclusion of sucrose, histidine or glycine, or their equivalents, in a monomeric protein composition significantly increases the stability and solubility of the protein composition by inhibiting the formation of polypeptide aggregates during frozen storage and repeated freeze/thaw manipulations. Thus, the present invention makes possible the stable frozen storage of monomeric protein compositions, and the methods of preparing such stable compositions.

In general, the monomeric protein compositions of the present invention are single-chain antigen-binding proteins. The compositions may contain other components in amounts which will preferably not detract from the preparation of the frozen storage-stable forms thereof. Moreover, the preferred monomeric single-chain antigen-binding protein compositions will be prepared using components of the type and in amounts acceptable for safe, effective pharmaceutical administration of the storage-stabilized product.

For the purposes of this application, "monomer" or "monomeric" refers to the a molecule having only a single peptide chain, regardless of the number of antigen-binding sites contained therein. Thus, the storage-stabilized monomeric single-chain antigen-binding protein of the present invention may be exemplified by a single chain molecule having one binding site, or by a multivalent antigen-binding molecule having more than one antigen-binding site, permitting bi- and multi-specific binding, so long as such multivalent antigen-binding molecules are monomeric proteins. However, it is the unwanted formation of polypeptide aggregates in a stored monomeric protein composition that is inhibited by the frozen storage-stabilizing methods of the present invention.

The terms "single-chain molecule" or "single-chain protein" are used interchangeably here. They are structurally defined as a first polypeptide, comprising the binding portion of the variable region of an antibody heavy or light chain, associated with a second polypeptide, comprising the binding portion of the variable region of an antibody heavy or light chain, the two polypeptides being joined by a peptide linker linking the first polypeptide and second polypeptide into a single polypeptide chain. The single polypeptide chain thus comprises a pair of variable regions connected by a polypeptide linker. The regions may associate to form a functional antigen-binding site, as in the case wherein the regions comprise a lightchain and a heavy-chain variable region pair with appropriately paired complementarity determining regions (CDRs). In such a case, the single-chain protein is referred to as a "single-chain antigen-binding protein" or "single-chain antigen-binding molecule." A similar single-chain antigen-binding protein comprising multiple pairs of heavy and light chain variable regions is also a part of this invention.

The variable regions may have unnaturally paired CDRs or may both be derived from the same kind of antibody chain, either heavy or light, in which case the resulting single-chain molecule may not display a functional antigen-binding site. Two or more such single-chain molecules may associate to form a multivalent antigen-binding protein. The single-chain antigen-binding protein molecule is more fully described in U.S. Pat. Nos. 4,946,778 and 5,260,203 both of which are incorporated herein by reference in their entirety.

The monomeric protein compositions stabilized by the present invention may be actually produced for the purpose of creating a frozen stock or they may be procured from whatever commercial or institutional source makes them available. The "single-chain antigen-binding proteins" may be produced by any process, including the process set forth in U.S. Pat. No. 4,946,778 (Ladner et al.).

The single-chain antigen-binding protein used to exemplify the stabilized monomeric protein compositions of the present invention include, for example, single-chain proteins comprising the CC49 $V_L$ region connected through the 218 linker polypeptide to the CC49 $V_H$ region (CC49/218). Many such single-chain antigen-binding proteins, including a variety of linker and domain combinations, have been described previously (Colcher et al., *J. Natl Cancer Inst.* 82:1191 (1990); Milenic et al., *Cancer Res.* 51:6363 (1991); Pantoliano et al., *Biochemistry* 30:10117 (1991); and Whitlow et al., *Protein Engng.* 6:989 (1993)), each of which is herein incorporated by reference if the description of such single-chain antigen-binding proteins is deemed relevant.

Without being bound by any particular theory, the inventors speculate on several models which can equally explain the phenomenon of multivalent aggregation observed as a result of frozen storage of monomeric protein compositions, and which becomes particularly evident following repeated freeze/thaw manipulations. Stabilization of a protein monomer appears to be enhanced by creating a suitable microenvironment surrounding the molecule. However, the invention is useful and operable to inhibit such aggregation, regardless of the precise mechanism behind the formation of polymeric aggregates or behind the effective method of monomeric protein stabilization.

"Frozen storage" refers to freezing and maintaining a previously aqueous monomeric protein sample at a temperature below 0° C., preferably −20° C. or lower.

"Freeze/thaw cycles" or "freeze/thaw manipulations" refer to known techniques for using a protein sample in frozen storage, wherein the temperature of the sample is raised to a level which will restore its aqueous state for a sufficient period of time to permit use of the sample, followed by freezing to a temperature below 0° C. and return to frozen storage, preferably at a temperature of −20° C. or lower.

In a preferred embodiment, the monomeric protein composition is storage-stabilized by the addition of sucrose, histidine or glycine. The sucrose, histidine or glycine additive concentration is between 0.1 and 20 mM, preferably formulated in a pharmaceutically acceptable buffer. More preferably the sucrose, histidine or glycine additive concentration is between 0.4 and 15 mM, most preferably between 0.4 and 10 mM, and often at approximately 10 mM. The invention further may include combinations of sucrose, histidine and/or glycine at the above concentration.

In the most preferred embodiment of the present invention, the monomeric protein composition is storage-stabilized by the addition of histidine at the above concentration.

Preferably the concentration of monomeric protein in the compositions of the present invention will range from about 0.1 mg/ml to about 10 mg/ml of stabilized solution. The ratio of sucrose, glycine or histidine to the monomeric protein in the composition of the present invention will be about 5 moles to about 400 moles for each 1 mole of monomer, preferably about 50 moles to about 350 moles for each 1 mole of monomer, more preferably about 100 moles to about 300 moles for each 1 mole of monomer, and most preferably about 150 moles to about 250 moles for each 1 mole of monomer. Often the ratio of sucrose, glycine or histidine to the monomeric protein in the composition of the present invention will be about 200 moles for each 1 mole of monomer. However, the exact ratio required for a particular combination of protein, formulation components, amino acid or mixture and prescribed storage conditions can be determined by simple experimentation, using the usual analytical techniques for protein activity or aggregation over the desired storage lifetime.

Suitable pH ranges for the preparation of the frozen-storage stabilized monomeric protein compositions are about 4 to about 9, preferably in the range of about 6 to about 8, more preferably in the range of about 6.7 to about 7.5. When the stabilized monomeric protein composition is intended for pharmaceutical use, the most preferred pH is in the physiologically acceptable range, i.e., about neutral.

In addition to sucrose, histidine or glycine, the stabilized monomeric protein compositions of the present invention also contain a compatible buffer system to maintain the acceptable pH levels. A preferred buffer system is a combination of sodium dibasic phosphate and sodium monobasic phosphate, for example, phosphate buffered saline (PBS).

Additionally, the improved, storage-stable, monomeric single-chain antigen-binding protein composition may optionally include one or more nonionic detergents, such as TWEEN 80 (Polyoxyethylene sorbitan), polysorbate 20, polysorbate 80, and the like, in amounts of from 0.001 to about 1%, to enhance the stability of the protein composition to freeze/thaw manipulations. Moreover, other pharmaceutically acceptable excipients, well known to those skilled in the art, may also form a part of such compositions. These may include, for example, various bulking agents, additional buffering agents, chelating agents, antioxidants, preservatives, cosolvents, and the like. Specific examples of such pharmaceutically acceptable excipients could include mannitol, trimethamine salts ("Tris buffer"), gelatin, human serum albumin or other polypeptides, various small peptides such as glycylglycine, and the like.

Aggregation of the monomers in a frozen-stored, monomeric protein composition can be measured by any method known in the art. Such methods include gel filtration chromatography to separate proteins on the basis of their molecular weight. A "gel" is a matrix of water and a polymer, such as agarose or polymerized acrylamide. The present invention encompasses the use of gel filtration HPLC (high performance liquid chromatography), as will be appreciated by one of ordinary skill in the art. Elution procedures are well known in the chemical and biochemical arts, as are methods of manual and automated fraction collection.

Other recognized methods of measuring aggregation include cation exchange chromatography, which is the general liquid chromatographic technique of ion-exchange chromatography utilizing anion columns well-known to those of ordinary skill in the art. The cations exchanged in the present invention are from the protein molecules. Since multivalent protein aggregates will have some multiple of the net charge of the single-chain antigen-binding protein, the aggregates are retained more strongly, and are thus separated from the single-chain molecules. A preferred cationic exchanger is a polyaspartic acid column.

Thus, a monomeric single-chain antigen-binding protein can be readily distinguished from an aggregate. However, those of ordinary skill in the art will realize that aggregation assays of the invention are not limited to any particular type of chromatography column, so long as it is capable of separating the two forms of protein molecules.

The use of the term "to inhibit aggregation" or "aggregation inhibited" when used to describe a composition of single-chain antigen-binding protein molecules, means the lack of a significant peak corresponding to an aggregated polymeric protein molecule when the composition is analyzed by, e.g., gel filtration chromatography Gel filtration HPLC chromatography (TSK G2000SW column from Toyo Soda, Tokyo, Japan) has been used to identify and separate monomeric single-chain and multivalent antigen-binding proteins. This procedure has been described by Fukano, et al., J. Chromatography 166:47 (1978).

A treated composition of the present invention in which the monomeric form is retained by more than 85%, and preferably by more than 90%, and most preferably by more than 94–95% of the protein composition (that is, having less than 5–6% aggregation) following frozen storage, would be considered to be "aggregation inhibited," or "storage-stabilized." In the same context, a composition retaining less than 70% of its original monomeric composition (that is, having more than 30% aggregation) following frozen storage is considered unstable.

EXAMPLES

The following working examples and references illustrate the invention in further detail, so that it may be more fully understood by one of ordinary skill in the art. However, these examples are given solely for the purpose of illustration, and should not be considered as expressing limitations unless so set forth in the appended claims.

Example 1—Effective Frozen-Storage Stabilization

To compare the effect of various additives on the stability of a frozen monomeric protein composition under repeated freeze/thaw cycles, a uniform set of single-chain antigen-binding protein samples was prepared from CC49/218 sF$_v$ (lot 93002-vial 5). The concentration of CC49/218 sF$_v$ (MW 27,000 d) in each sample was 1.45 mg/ml in sodium phosphate buffered saline (PBS) at pH 7.3.

The control sample was maintained at the starting concentration of CC49/218 sF$_v$ in the PBS buffer without additive. Each test sample was mixed with one of the following: sucrose 10 mM, glycine 10 mM, or histidine 0.4 mM, 0.8 mM or 10 mM. The additives were prepared using the same PBS, pH 7.3, as was used to prepare the samples. The samples were then frozen and maintained at −20° C., or lower. Periodically, as indicated in Table 1, the samples were thawed at room temperature and assayed to determine whether the monomeric single-chain peptides had formed polymeric aggregates as a result of the freeze/thaw procedure.

Aggregation was measured by a gel filtration chromatography column (TSK-Gel G3000SWXL, 7.8×300 mm with a guard). The buffer used to elute the sample from the exclusion column was: 0.05M MOPS, 0.2M Na$_2$SO$_4$, 0.02% NaN$_3$ at pH 7.0. The flow rate was maintained at 0.5 ml/min.

The effectiveness of each additive as a aggregation-inhibiting storage-stabilizing agent is set forth in the following table, Table 1:

TABLE 1

The Effect of Selected Additives on the Stability Monomers of CC49/218 sF$_v$ Following Frozen Storage

| Additive | Conc. | # Days Frozen | # Freeze/Thaw Cycles | % Monomer |
| --- | --- | --- | --- | --- |
| control in PBS | starting | 0 | 0 | 95.4 |
| PBS | 1× | 1 | 1 | 84% |

TABLE 1-continued

The Effect of Selected Additives on the Stability
Monomers of CC49/218 sF$_v$ Following Frozen Storage

| Additive | Conc. | # Days Frozen | # Freeze/Thaw Cycles | % Monomer |
|---|---|---|---|---|
| PBS | 1× | 4 | 2 | 59.2% |
| PBS | 1× | 5 | 3 | 44% |
| PBS | 1× | 6 | 4 | 37% |
| Sucrose | 10 mM | 4 | 1 | 91% |
| Sucrose | 10 mM | 5 | 2 | 87% |
| Sucrose | 10 mM | 7 | 3 | 87% |
| Sucrose | 10 mM | 21 | 4 | 94% |
| Glycine | 10 mM | 4 | 1 | 88% |
| Glycine | 10 mM | 5 | 2 | 90.5% |
| Glycine | 10 mM | 7 | 3 | 92% |
| Glycine | 10 mM | 21 | 3 | 94% |
| Histidine | 10 mM | 1 | 1 | 94% |
| Histidine | 10 mM | 5 | 3 | 94% |
| Histidine | 0.8 mM | 6 | 4 | 93.5% |
| Histidine | 0.4 mM | 6 | 4 | 89.7% |

Thus, the frequency of freezing had a dramatic effect on the aggregation of the sample. The stabilizing effect of each additive was more clearly seen after a repeated series of freeze/thaw manipulations.

Example 2—Additive Useful Only for Short-Term Frozen Stabilization of a Monomer

An additional set of samples was prepared from CC49/218 sF$_v$ as described in Example 1. Also as described in Example 1, each sample was supplemented with one of the following additives, prepared in the same PBS buffer as the sample buffer, at pH 7.3: glycerol 10%, mannitol 10 mM, cysteine 10 mM, TWEEN 80 (Polyoxyethylenesorbitan) 0.1%, a combination of TWEEN 80 (Polyoxyethlenesorbitan) 0.1% and arginine 10 mM, or a combination of TWEEN 80 (Polyoxyethlenesorbitan) 0.1% and mannitol 10 mM. The control sample was again CC49/218 sF$_v$ maintained at the starting concentration in PBS buffer, pH 7.3, without additives.

The treated samples were frozen and maintained at −20° C. or lower. Periodically, as indicated in Table 2, the samples were thawed at room temperature and assayed to determine whether the monomeric single-chain peptides had formed unwanted aggregates as a result of the freeze/thaw procedure.

As in Example 1, aggregation was measured by a gel filtration chromatography column (TSK-Gel G3000SWXL, 7.8×300 mm). The elution buffer was: 0.05M MOPS, 0.2M Na$_2$SO$_4$, 0.02% NaN$_3$ at pH 7.0, and the flow rate was 0.5 ml/min.

The effectiveness of each additive as a aggregation-inhibiting storage-stabilizing agent is set forth in the following table, Table 2:

TABLE 2

The Effect of Selected Additives on the Stability
of Monomers of CC49/218 sF$_v$ Following Frozen Storage

| Additive | Conc. | # Days Frozen | % Monomer | Observation* |
|---|---|---|---|---|
| control | starting | 0 | 95.4% | |
| glycerol | 10% | 1 | 95% | ppt seen at 2nd thaw |
| mannitol | 10 mM | 1 | 84% | ppt seen at 2nd thaw |
| mannitol 10 mM, TWEEN 80 (Polyoxyethylene-sorbitan) | 0.1% | 1 | 73.8% | ppt seen at 2nd thaw |
| arginine 10 mM, TWEEN 80 (Polyoxyethylene-sorbitan) | 0.1% | 1 | 88.1% | ppt seen at 2nd thaw |
| cysteine TWEEN 80 (Polyoxyethylene-sorbitan) | 10 mM | 1 | 81% | low molecular weight degradation products seen |
| TWEEN 80 (Polyoxyethylene-sorbitan) | 0.1% | 1 | 70% | ppt seen at 2nd thaw |

*ppt = precipitate; indicating substantial (>30%) visible aggregation of the monomers Example 3—Additives Ineffective for the Frozen-Storage Stabilization of a Monomer An additional set of samples was prepared from CC49/218 sF$_v$ as described in Example 1. Also as described in Example 1, each sample was supplemented with one of the following additives: tryptophane, trehalose, lysine, lactose, glutamic acid, glucose, polyethylene glycol (PEG) and PLURONIC F-68 (Polyoxypropylene-polyoxyethylene block copolymer) (obtained from Sigma Chem., St. Louis, Mo.). The additives were each prepared at a concentration of 10 mM using the same PBS buffer as the sample buffer, at pH 7.3. Following treatment, the samples were frozen and maintained at −20° C. or lower.

As in Example 1, the frozen samples were thawed at room temperature, and aggregation of the monomeric single-chain antigen binding proteins was measured by a gel filtration chromatography column (TSK-Gel G3000SWXL, 7.8×300 mm). The elution buffer was again: 0.05M MOPS, 0.2M Na$_2$SO$_4$, 0.02% NaN$_3$ at pH 7.0, with the flow rate was maintained at 0.5 ml/min.

In each case, the addition (10 mM: tryptophane, trehalose, lysine, lactose, glutamic acid, glucose, PEG or PLURONIC F-68 (Polyoxypropylene-polyoxyethylene block copolymer) failed to stabilize the monomeric protein composition against significant aggregation of the molecules as a result of repeated freeze/thaw cycles. Aggregation, as measured by gel filtration chromatography column as described in Example 1, was found in each case to unacceptably exceed 30% of the monomeric composition.

Although the present invention has been described with reference to the presently preferred embodiments, the skilled artisan will appreciate that various modifications, substitutions, omissions, and changes may be made without departing from the spirit of the invention. Accordingly, it is intended that the scope of the present invention be limited only by the scope of the following claims, including equivalents thereof.

What is claimed is:

1. A composition comprising a single-chain antigen-binding protein in a frozen aqueous solution and a compound selected from the group consisting of sucrose, histidine and glycine; wherein the compound is present in said aqueous solution at a concentration of 0.1 to 20 mM and wherein said composition is not lyophilized; whereupon following a freeze/thaw cycle, said composition retains more than 85% of said single-chain antigen-binding protein in a monomeric form.

2. The composition of claim 1, wherein the compound is sufficient to inhibit aggregation of the single-chain antigen-binding protein during freeze/thaw cycles.

3. The composition of claim 2, wherein said compound is sucrose.

4. The composition of claim 2, wherein said compound is glycine.

5. The composition of claim 2, wherein said compound is histidine.

6. A non-lyophilized composition, comprising a single-chain antigen-binding protein in aqueous solution, wherein said composition is produced by a method comprising:
   a) adding before freezing a stabilizing amount of a compound selected from the group consisting of: sucrose, histidine and glycine, to a solution containing said single-chain antigen binding protein
   b) freezing said composition; and
   c) thawing said composition
wherein said composition is an aqueous solution after thawing and said composition retains more than 85% of said single-chain antigen-binding protein in a monomeric form.

7. The composition of claim 6 wherein said compound is sucrose.

8. The composition of claim 6 wherein said compound is glycine.

9. The composition of claim 6 wherein said compound is histidine.

10. A composition comprising (i) a single-chain antigen-binding protein in aqueous solution, ii) a compound selected from the group consisting of sucrose, histidine and glycine wherein said compound is present in said aqueous solution at a concentration of 0.1 to 20 mM and (iii) a buffer wherein said composition is in an aqueous solution after thawing and said composition retains more than 85% of said single-chain antigen-binding protein in a monomeric form.

11. The composition of claim 10, wherein said compound is sucrose.

12. The composition of claim 10, wherein said compound is glycine.

13. The composition of claim 10, wherein said compound is histidine.

* * * * *